United States Patent [19]

Brain

[11] Patent Number: 5,896,858
[45] Date of Patent: Apr. 27, 1999

[54] ENDOTRACHEAL-TUBE GUIDANCE SYSTEM WITH EPIGLOTTIS-ELEVATING FEATURE

[76] Inventor: Archibald Ian Jeremy Brain, Sandford House Fan Court Gardens, Longcross Road, Chertsey, Surrey, United Kingdom, KT16 ODJ

[21] Appl. No.: 08/826,563

[22] Filed: Apr. 4, 1997

Related U.S. Application Data

[63] Continuation of application No. 08/641,957, May 2, 1996, abandoned.

[30] Foreign Application Priority Data

Oct. 3, 1995 [GB] United Kingdom ............ 9520139
Nov. 23, 1995 [GB] United Kingdom ............ 9523964

[51] Int. Cl.$^6$ .................................................. A61M 16/00
[52] U.S. Cl. .............................. 128/207.15; 128/200.26; 604/96
[58] Field of Search ............. 128/207.15, 207.14, 128/207.16, 200.26, 206.26; 604/96, 100, 174, 164

[56] References Cited

U.S. PATENT DOCUMENTS 5,632,271  5/1997  Brain .................... 128/207.15
5,653,229  8/1997  Greenberg ............. 128/207.15
5,682,880  11/1997  Brain .................... 128/207.15

Primary Examiner—John G. Weiss
Assistant Examiner—Charles W. Anderson
Attorney, Agent, or Firm—Hopgood, Calimafde, Kalil & Judlowe

[57] ABSTRACT

An artificial airway device to facilitate a patient's lung ventilation comprises an airway tube and a laryngeal mask at one end of the tube. The mask is of generally elliptical configuration, with an inflatable peripheral cuff of flexible material around the edges of the mask, for sealed support of the mask around the inlet to the patient's larynx. The mask has an aperture through which the airway tube opens into the interior of the mask. The mask also comprises a longitudinally directed bar, extending across the mask aperture, from the central upper edge or rim of the mask aperture, to which it has effectively a hinged attachment, to the posterior rim of the mask aperture, at which the bar is free. The hinged mounting of this bar is so positioned at longitudinal offset from the distal end of the mask (which locates in the upper sphincter or oesophageal inlet) that the introduction of an inserted endotracheal tube will automatically engage and swing the bar backward into camming engagement with the epiglottis, thus easily folding the epiglottis backward against the wall of the laryngeal inlet and permitting undeflected insertional passage of the endotracheal tube to and through the laryngeal inlet, and permitting undeflected insertional passage of the endotracheal tube to and through the laryngeal inlet.

33 Claims, 4 Drawing Sheets

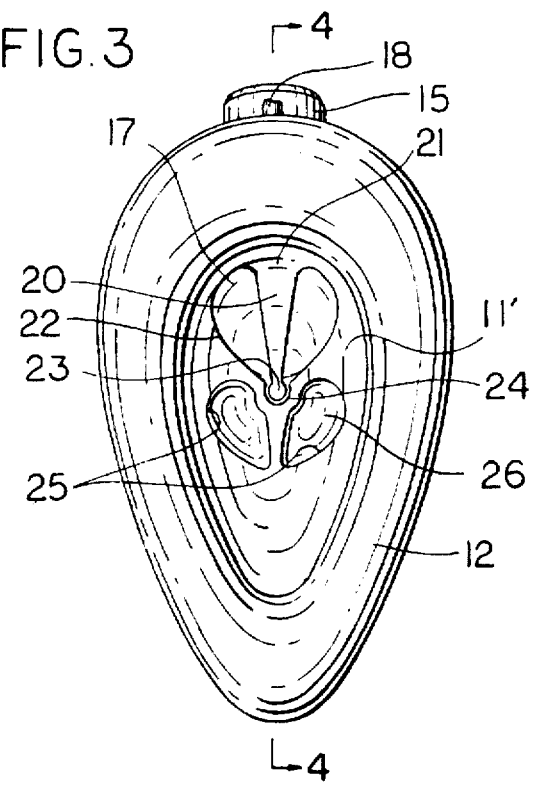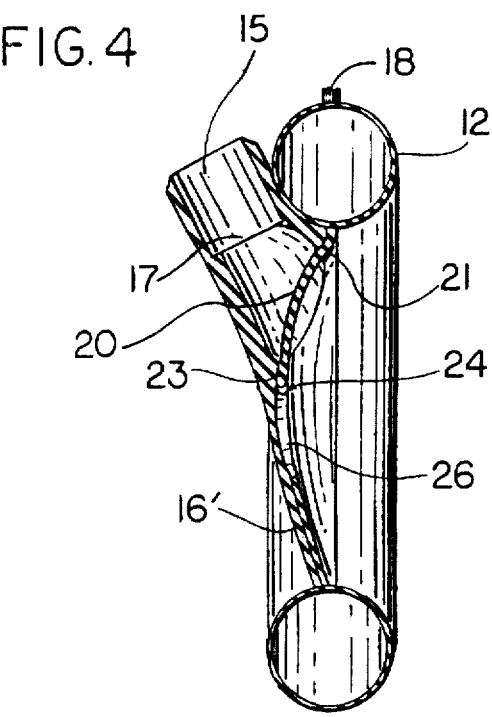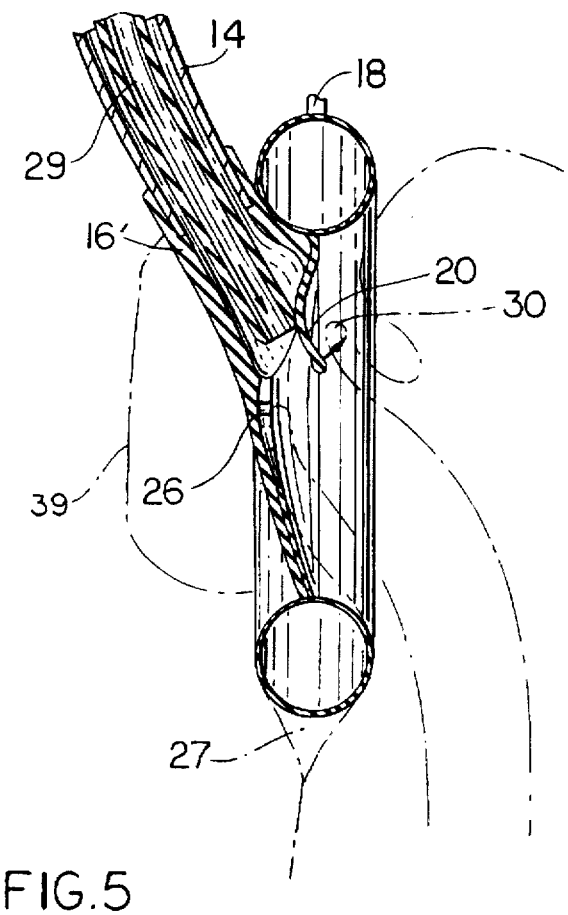

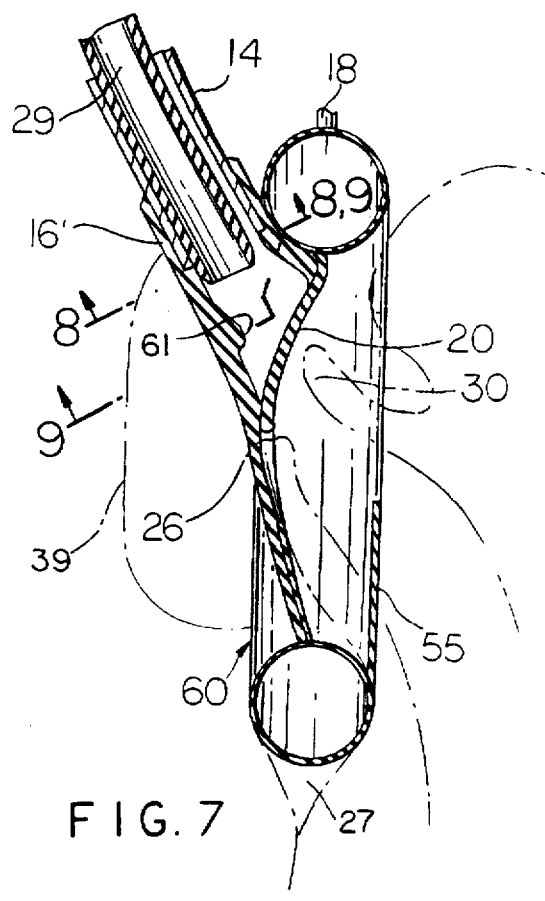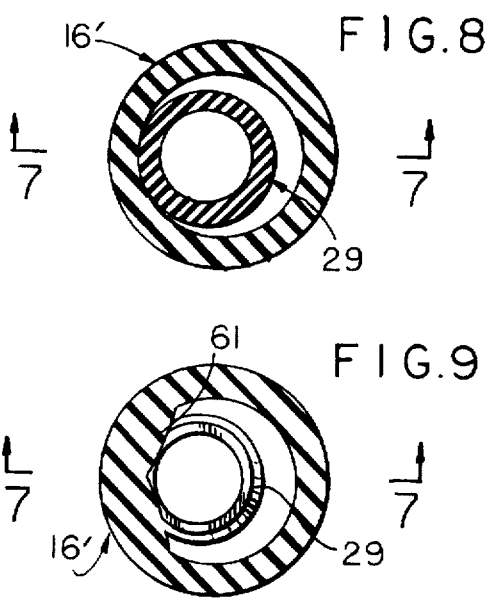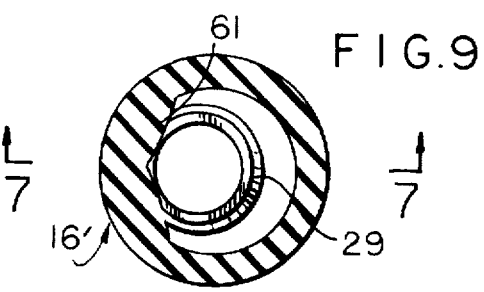

ENDOTRACHEAL-TUBE GUIDANCE SYSTEM WITH EPIGLOTTIS-ELEVATING FEATURE

RELATED CASE

This application is a continuation of copending original application, Ser. No. 08/641,957, filed May 2, 1996 now abandoned.

BACKGROUND OF THE INVENTION

This invention relates to an endotracheal-guidance system, such as an artificial airway device, or laryngeal-mask airway (LMA) device, of the type that finds use in anaesthetic procedures.

Patent No. GB 2,205,499 describes a miniature mask attached to a tube designed to fit into the lower throat as a means of securing the airway of an unconscious patient during anaesthesia. Such devices have met with quite remarkable success and are currently used in some 50 percent of general anaesthetic procedures in the United Kingdom. The use of such masks continues to spread throughout the world. The principal advantages associated with the use of such a mask are the simplicity of its installation and uses, the freeing of the anaesthetist's hands, and the lack of trauma to airway structures, as compared with the conventional and more traditional endotracheal tube (ET).

An important limiting factor in the use of the LMA device is its failure to adequately protect the lungs of an unconscious patient when regurgitation of stomach contents unexpectedly occurs. An endotracheal tube (ET), once placed in the windpipe, is still considered to be the definitive solution to this problem in patients at risk. However, it is sometimes difficult or even impossible to correctly position an ET owing to anatomical factors which may be unpredictable, and there is therefore always a risk that intubation of the windpipe will fail. This has resulted in death or brain damage of previously completely healthy people. While the LMA device can prevent this disaster, if there is also a risk of stomach contents entering and damaging the lungs (for example, in the case of anaesthesia for Caesarian Section), then most practitioners will want to subsequently achieve insertion of an ET even if disaster has been averted by supplying oxygen to the lungs via an LMA device.

This requirement has led to the design of a special LMA device (see, for example, U.S. Pat. No. 5,303,697) adapted to serve as guidance means to allow insertion of the appropriate size of ET. Indeed, the standard LMA device will permit insertion of a rather small-size ET, although the technique is not always successful, and it may subsequently be necessary to exchange the small ET for a larger one; such an exchange is a somewhat complicated and often difficult procedure, which is not without risk to the patient. The reason why it is not always possible to pass an ET through an LMA device into the windpipe (trachea) can only be understood by reference to an anatomical structure known as the epiglottis, which is in effect a cartilaginous shield attached to the upper border of the opening into the larynx (the glottis).

The epiglottis has an important function in directing the flow of food or drink when swallowed so that the flow does not accidentally spill into the windpipe or trachea via the glottic opening. The epiglottis is a hinged structure which swings down somewhat like a visor over the glottis during the action of swallowing. When the LMA device is placed in the lower throat (hypopharynx), the epiglottis is pushed forward, and its rim is held away from the LMA mask aperture by two bars, the mask-aperture bars (MABs). The MABs prevent the flap-like epiglottis from folding down to obstruct the passage of gas through the mask aperture, and in practice they fulfil this function reliably without traumatising the epiglottis. However, in order to pass an ET through the mask aperture of the LMA and into the glottis and trachea, it is sometimes necessary for the epiglottis to be lifted further upwards (swung further out of the way of the aperture) than can be achieved with the current design of MABs. Indeed, the MABs are not designed to force the epiglottis away from its normal anatomical neutral position in the airstream, and it is therefore not surprising that it may be difficult to pass a tube under the epiglottis to get it into the glottic opening even though gas may be passing freely through the LMA into the patient's lungs.

Normally, this problem can be solved by use of a fibrescope, which is a bendable light source and telescope which permits the anaesthetist to directly view the structures described and then thread an ET over the fibrescope and into the trachea. However, such direct-viewing equipment is expensive, and the procedure may be time-consuming. In matters pertaining to management of the airway of unconscious patients, time is of the essence, in that four minutes without oxygen is enough to cause brain damage.

MABs of current design consist of twin parallel bars of soft silicone material which (1) are sufficiently pliable to readily deflect and thus to allow passage of an object up to the diameter of the mask aperture itself, but which (2) are firm enough to resist penetration of the aperture by the epiglottis, which is caught up against them, rather like a fish caught in a net. Two bars have been used rather than some other number such as three or one, so that any tube passing through will not encounter a central bar and will thus not be deviated to one side (of a central bar), while a greater number than three bars would unnecessarily increase resistance to gas flow.

BRIEF STATEMENT OF THE INVENTION

It is a first principal object of the invention to provide an improved LMA construction which will materially reduce the chance of epiglottis interference with the path of LMA-guided insertion of an endotracheal tube (ET) or other LMA-guided instrumentation. It is a second principal object of the invention to provide an improved guidance system for guided insertion of an endotracheal tube (ET) or other guided instrumentation, wherein a structural feature at the distal end of the guidance system will materially reduce the chance of epiglottis interference with the path of guided insertion of the system-guided instrumentation.

A specific object is to meet the first above-stated object with an LMA construction, wherein a displaceable part of the LMA can be automatically so actuated by the insertional approach of an ET or other LMA-guided instrument, that the epiglottis is caused to be displaced out of the insertional path of the ET or other LMA-guided instrument.

Another specific object is to provide improved LMA structure of the character indicated with means for more correctly directing the advancing distal end of ET or other airway-guided instrumentation after it has emerged from the airway tube of the LMA.

A further specific object is to provide improved LMA structure which can better assure that an ET or other LMA-guided instrumentation intended for passage to or through the glottic opening cannot be inadvertently inserted into the oesophagus or the hypopharynx.

Still another specific object is to provide in an LMA device a means whereby an epiglottis which happens to have been downfolded in the course of mask insertion (thus preventing passage of an endotracheal tube through the glottic aperture) may nevertheless be manipulated as to reverse the downfolded orientation and thus render the glottic opening accessible for intubating passage through the mask aperture.

A general object is to meet the above objects with a construction which involves minimal incremental cost. Another general object is to meet above objects with an LMA construction which will provide greater acceptability of the LMA, for enhanced safety to the patient, as when ET insertion is in the hands of insufficiently-skilled, emergency medical-service personnel.

The present invention meets the foregoing objects and, in its preferred application to an LMA, is based upon an appreciation that an MAB construction which permits the epiglottis to be swung out of the way of an approaching ET will result in certain advantages.

In a preferred artificial airway or LMA device of the present invention, a single relatively more rigid but still flexible bar replaces the current soft twin bars in the mask aperture. This single bar extends longitudinally and is central across the mask aperture, and it is fixed only to the upper or anterior rim of the aperture, while its lower or posterior end is free, allowing the bar to be compliantly deflected and bent outward if it is pushed from within the aperture. Since the rim of the epiglottis normally lies transversely across the aperture, a single deformable but sufficiently rigid bar that is free to move at its lower end can act as a lever to lift the epiglottic rim away from the aperture when such a bar is pushed forward from within the aperture. The free end of such a bar does not contact or become entangled with the epiglottic rim during insertion of the LMA device because it is designed to lie flush with the bowl-shaped interior of the mask body along which the epiglottic rim must slide in the process of LMA installation in the patient.

The precise disposition of the single flexible bar with respect to the aperture will depend to some extent on the nature of any instrument to be passed through the LMA device. For example, the bar may be disposed centrally over the length of the aperture (i.e., longitudinally with respect to the mask as a whole) in which case it preferably has a width of up to approximately 6 mm, which has been found to be a maximum practical width that does not cause a significant reduction in air flow through the aperture. Suitably, the bar has a convex surface to the interior of the airway tube. Such a surface will generally ensure that the bar cooperates with the leading end of any inserted instrument, for example, a fibrescope passed down the airway tube and through the aperture; and the bar is pushed downward by such a leading end, in order to lift the epiglottic rim away from the aperture instead of the bar being merely distorted to one side by the leading end. Were the inserted instrument to cause distortion to one side, there would be no way to swing the epiglottis away from the aperture.

In the case, however, of an endotracheal tube being passed through the airway tube, it must be borne in mind that the leading end of such a tube is conventionally bevelled at an angle of 60 degrees to the transverse. This means that the leading end of that tube is positioned at 30 degrees with respect to the longitudinal mid-line of the aperture and consequently the bar in its at-rest position is preferably disposed at an angle of substantially 30 degrees to the longitudinal mid-line, being attached to the rim of the aperture, at its anterior end, and free at its other end. In this way, the aperture bar is able to cooperate with the leading end of the endotracheal tube and to lift the epiglottic rim away from the aperture as the endotracheal tube is passed through the aperture.

A further and preferred feature of the LMA device of the present invention is the provision of two local depressions in the concave bowl-shaped body of the mask; the depressions are positioned for correspondence to and reception of the bilateral swellings (arytenoid cartilages) which exist on either side of the lower rim of the human glottis; thus, when the LMA device is correctly positioned in the throat, those swellings lie snugly in the depressions and are not compressed or pushed forward by the relatively unyielding surface of the mask body.

It is noted that to date, the concave profile of LMA constructions has not taken into account the bilateral anatomical presence of the arytenoid cartilages, which in certain cases can be compressed or pushed forward by the mask body, in the course of LMA installation in a patient. Thus, by providing the bilateral local concavities as a contoured feature of the mask bowl, it becomes possible (a) to prevent the arytenoid cartilages from being pushed forward (thereby to avoid a possible cause of respiratory obstruction), and (b) to allow the arytenoid cartilages to sink below the line of approach of any tube inserted into the mask via the mask aperture, as for example when intubation of the trachea is attempted, using the LMA device as a guide. In such situations, it has not been uncommon for the arytenoid cartilages to be traumatised by the advancing tube tip colliding with one or both of the arytenoid cartilages.

A further problem may also commonly arise when attempting intubation through an LMA device, namely, that if the advancing tube tip strikes one of the arytenoids, the tube tip may consequently be diverted or deflected backward (posteriorly), thus locally breaking the inflated LMA seal to the laryngeal inlet and passing into the oesophagus instead of the trachea. If this happens, it may be difficult and therefore confusing not to know that the tube tip has or has not entered the laryngeal orifice; such confusion may be life-threatening since the anaesthetist may start to ventilate the stomach in the belief that the lungs are being ventilated. However, the above-noted provision of local concavities to receive the arytenoid cartilages is seen as a feature which naturally reduces the risk of arytenoid-cartilage misdirection of an endotracheal tube.

The airway tube which carries the laryngeal mask at one end is generally of relatively stiff but flexible material to enable its manipulation through the patient's mouth and throat until the mask is correctly positioned around the laryngeal inlet. In a further aspect of the invention, however, the airway tube may be instead of a softer and more pliable construction which then preferably includes, suitably along its outer arcuate radius of curvature, a channel which accommodates a rigid handle extending into and along the outer radius of the airway tube at least during insertion of the device into the patient's throat. After the airway device has been properly positioned, the handle may be removed, thus leaving an open-ended channel which may extend along the whole length of the airway tube, with an opening into the mask through the airway aperture; the thus-open channel may then be used for aspirating any unwanted fluids or secretions, or it may be used to pass a removable fibrescope into the interior of the mask. Such a construction is described in greater detail in International Patent Application No. PCT/GB95/01292.

BRIEF DESCRIPTION OF THE DRAWINGS

The present invention will be described in greater detail, in conjunction with the accompanying drawings, in which:

FIG. 3 is a plan view similar to FIG. 1, but showing an LMA device according to the invention;

FIG. 4 is a longitudinal section similar to FIG. 2, but taken generally in the plane 4—4 of FIG. 3;

FIG. 5 is a longitudinal section of the LMA device of FIGS. 3 and 4, positioned in a patient's airway during insertion of an endotracheal tube;

FIG. 7 is a longitudinal section to show a further modified LMA device of the invention;

FIG. 8 is a simplified cross-section, to an enlarged scale, taken at 8—8 of FIG. 7;

FIG. 9 is a view similar to FIG. 8, but taken at 9—9 of FIG. 7;

DETAILED DESCRIPTION

Figure 1:
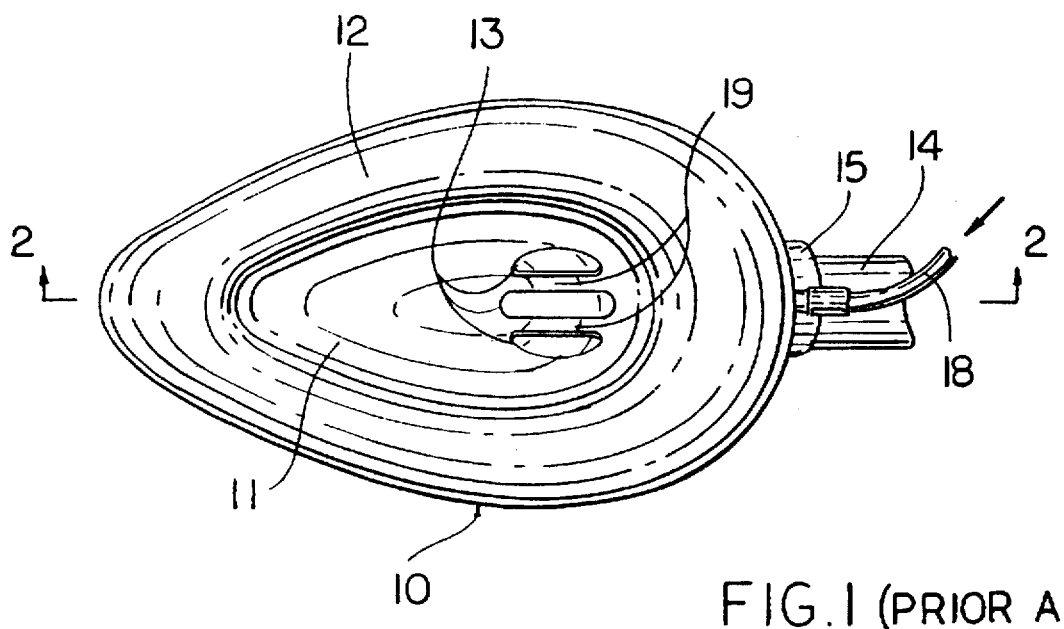
FIG. 1, labelled "PRIOR ART", is a plan view of a conventional LMA device, showing the side which is to face and to peripherally engage a patient's laryngeal inlet.
Figure 2:
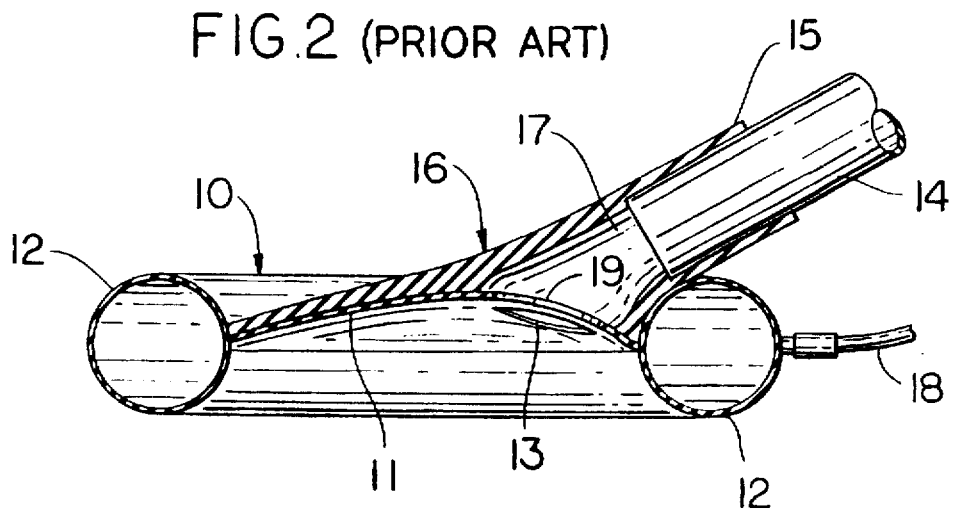
FIG. 2 is a simplified longitudinal section, also labelled "PRIOR ART", and taken generally in the plane 2—2 of the prior-art device of FIG. 1.

In the drawings, FIGS. 1 and 2 are labeled "PRIOR ART", to show a conventional LMA device 10 with its mask body or bowl 11, within an inflatable generally elliptical ring 12 which, when inflated as shown, is configured to establish a peripherally sealed engagement of the device 10 to a patient's laryngeal inlet. The mask body or bowl 11 separates the laryngeal side of the LMA from the pharyngeal side, and provides three apertures 13 for exclusive communication of an airway tube 14 via a patient's mouth and throat to an airway-inlet connecting formation 15 on the pharyngeal side of the mask. As shown, a backing plate 16 has the inlet formation 15 and provides not only a concave surface to which the mask body or bowl 11 is fitted, but also a discharge passage 17 directly aligned for air or gas flow passage through apertures 13 and into the laryngeal side of the mask. Inflation air is supplied to inflate ring 12 via a flexible tube 18 which will be understood to extend to suitable inflation/deflation means (not shown) and to include a check valve (also not shown), which serves to retain inflation of ring 12 once the LMA has been installed, and which also serves selectively to retain the deflated condition of ring 12 in the course of insertion of the LMA into installed position and in the course of extracting the LMA from installed position.

As noted above, the three apertures 13 in the mask body 11 are defined by two spaced, parallel, longitudinally extending bars 19 which span the discharge end of passage 17 in the backing plate 16. These bars are at bilateral offsets from the central plane of symmetry of the LMA, namely, the section plane in which FIG. 2 is taken. These bars 19 are relatively softly compliant, so as to yield symmetrically outward in the circumstance of a correctly aligned endotracheal-tube insertion via the airway tube 14, and also so as to prevent the patient's epiglottis from blocking air passage through the mask. The material of mask 11 and of inflatable ring 12 is a relatively thin and flexible elastomeric, customarily 30-durometer silicone rubber of 1-mm thickness. The backing plate 16 may be of the same material, but moulded to greater thickness, as suggested by sectioning in FIG. 2, wherein relative stiffness of the backing plate is the result of greater thickness.

FIGS. 3 and 4 of the drawings illustrate the invention and are intentionally drawn to correspond with FIGS. 1 and 2, to permit comparison of the invention with the prior art. The parts of FIGS. 3 and 4, which may be identical to those of FIGS. 1 and 2, are shown with the same reference numerals and therefore need not be redescribed. The principal difference in FIGS. 3 and 4 is that the distal or discharge end of air passage 17 within the backing plate 16' is traversed by a single central longitudinally extending bar formation 20 which may be an integrally formed part of the mask body or bowl 11', the integral connection of bar formation 20 with the rest of the mask body or bowl 11' being at the upper or proximal portion of the rim 21 of the otherwise open generally circular cut-out 22 which so registers with the discharge end of passage 17 that bar 20 effectively divides the discharge end of passage 17 into two smaller openings which are images of each other, on laterally opposite sides of the section plane 4—4. The bar 20 is preferably of the same elastomeric material as that of mask body 11', but bar 20 is more thickly formed, for less softly compliant deformability, being effectively hinge-mounted at 21 and desirably stiff enough to retain its arcuate shape, which is apparent in the at-rest position shown in FIG. 4. In this at-rest position, the lower or free end 23 of bar 20 is locally expanded and thickened to seat against material of the backing plate 16', with clearance from mask 11' contact, at a small distal-end cutout feature 24 of the larger cutout opening 22.

FIGS. 3 and 4 further show preference that mask body 11' be provided with two further openings 25 which register with two local recesses 26 in the concave curvature of backing plate 16'. These local recesses receive and locate the patient's arytenoid cartilages when the LMA of FIGS. 3 and 4 is installed in a patient.

FIG. 5 illustrates use of the LMA of FIGS. 3 and 4, when installed in a patient, with the distal end of the LMA in inflated engagement with the upper sphinctral region 27 of the patient's oesophagus. An endotracheal tube 29 is shown in the process of insertion within airway tube 14, with its distal end in camming engagement with the convex outer arc of bar 20. It will be understood that to get to this point the epiglottis will have been actively engaged to the concave arcuate profile of bar 20. To show such epiglottis engagement would be too distracting in the drawing, but a light-phantom showing 30 of the epiglottis in its ultimately bent deflection was chosen in FIG. 5, because ET passage through the mask opening 22 will be seen to entail further deflection of bar 20, to the extent of holding the epiglottis 30 in its position of maximum deflection; and to show the deflected position of bar 20 would tend to confuse the drawing of FIG. 5. Upon a retracting displacement of the endotracheal tube 29, the camming displacement of bar 20 is withdrawn, to allow bar 20 to restore its at-rest position of free-end arrest by renewed local abutment with backing plate 16'. In this at-rest position, the upwardly bowed arc of bar 20 conforms with adjacent contouring of mask 11', so that the function of preserving an airway passage against blockage by the epiglottis remains as before.

It is noted that the effectively hinged-bar arrangement which has been described will necessarily have to be at such longitudinal offset from proximal and distal ends of the LMA as will properly fit the LMA-size appropriate to the patient's size requirements. This is because LMA-size selection appropriate to the estimated size of the patient's pharynx is important to proper use of the LMA. Conventionally, a range of five LMA sizes is available from which to make the selection. Properly selected, the inserted LMA will locate at its distal end in the upper sphincter of the oesophageal inlet, as schematically suggested at 27 in FIG. 5. This being the case, the more proximal location of inflated-ring (12) engagement to the laryngeal inlet is automatically determined such that the hinged bar 20 will necessarily be positioned for ET-deflected engagement to displace the epiglottis out of the path of ET displacement, and with unhindered passage through the now-enlarged single aperture 22.

More particularly, and preferably, the bar 20 is composed of a stronger (firmer) material than the material of mask 11', and bar 20 should be relatively stiff except for its flexibly compliant hinge-like connection 21 to the upper center of the rim of aperture 22. Its other end 23 is preferably widened to form a flattened club-shape which in its at-rest position is nested in the "stop" recess or depression 24, of corresponding contour formed within the area of the mask body or bowl 11', adjacent the lower part of the rim of the mask aperture 22. FIGS. 4 and 5 further show a preference that depressions 26 be formed in the backing plate 16' (and mask bowl 11') on each side of the depression 24 to accommodate corresponding bulges of the arytenoid cartilages when the device is in place in a patient.

Figure 6:
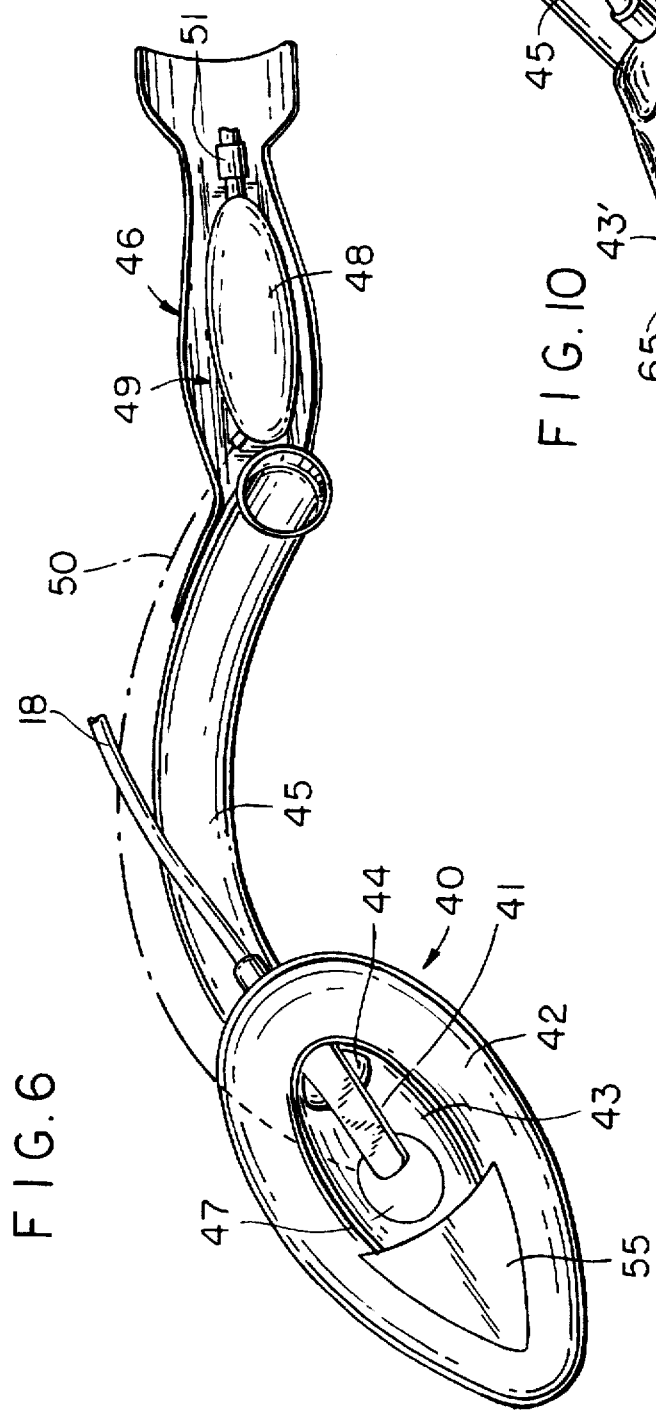
FIG. 6 is a perspective view of a modified LMA device of the invention.

FIG. 6 shows a modified LMA device with certain features of safety and convenience, enabling correctly guided passage of an ET or the like instrument that is to be guided solely into alignment for entry in and/or passage through the glottic opening. In FIG. 6, the laryngeal side of mask 40 is seen to feature a bar 41 which is compliantly suspended from the proximal end of the inner circumferential profile of the inflatable ring 42, it being noted that the thin flexible domed and apertured body member (as at 11 in FIGS. 1 and 2) has been omitted, as unnecessary in FIG. 6. Thus, the open end 44 of the airway tube connection is viewable within the bowl concavity in FIG. 6. The airway tube 45 is rigid, being a bent stainless steel tube, with a proximal end adapted for conventional service by an external source (not shown) of air or gas. At its outer end, a handle 46 is shaped for ready grasp and manipulation.

It is a feature of the embodiment of FIG. 6, that a locally inflatable device 47 within the concavity of the bowl of backing-plate member 43 is selectively operable to inflate into the path of guided passage of an ET or other instrumentation introduced via airway tube 45. The inflatable device is suitably a small balloon (or diaphragm) of elastomeric material forming part of a second closed pneumatic system which is independent of the air-inflation/deflation system 18 which serves the inflatable ring 42 of the mask. This second closed system includes a small, somewhat elongate actuating means in the form of a balloon member 48 which is conveniently fixed in an elongate concavity portion 49 of handle 46. A sealed flexible tube 50 is schematically shown to interconnect the two balloons 46, 48, and this second closed system is "closed" by check-valve means 51 which retains second-system air, the level of air pressure being sufficiently low that in the absence of the operator's squeezing of balloon 48, there will be no change in the normally low profile of balloon 47. On the other hand, an ET device which has been introduced via airway tube 45 and which has advanced (a) into deflecting contact with bar 41, and (b) into lapped register with balloon 47, is subject to such selectively variable controlled deflection of the distal end of the endotracheal tube as will enable correct alignment of the ET with the glottic opening, while also deflecting the epiglottis out of the way. If the inserted ET carries its own fibrescope (not shown), one can inspect via the distally fed end of the ET just how well the ET is aligned with the glottic opening through which it is expected to pass, and simple application of finger pressure at 48 in the grip of handle 46 will enable assurance of the instantaneously deflected correct ET alignment.

FIG. 6 additionally shows a feature of safety to the patient, in that a generally triangular skirt 55 of elastomeric sheet material is continuously bonded to adjacent segments of inflatable ring 42, along distally convergent sides of the skirt, so as to define a proximally open pocket, between skirt 55 and the distal-end region of the bowl concavity of the mask. If by chance an inserted ET device happens to emerge from the distal end 44 of airway tube 45 at an insufficiently elevated angle to clear the proximal end of the pocket, the pocket provides a trap, to foreclose further insertional advance of the ET, thus avoiding inadvertent ET passage to the oesophagus.

In FIG. 6, it will be understood that the displacement of air required for the described selective operation of inflatable device 47 is indeed small, so that a small-diameter flexible tube will serve the purposes of the connection 50 which completes the second inflatable system. Even so, the relatively great volume of balloon 48 compared to that of inflatable device 47 assures that such force as is required to deflect the distal end of an ET tube is more than amply available for selective use.

Elegant as it may be, to be able to selectively align an ET or other instrument for correct passage via an LMA, the technique and apparatus of FIG. 6 may be deemed to be relatively expensive, even though the technique is flexibly and uniquely adaptable to such variations as may exist in the difference between the inside diameter of airway tube 45 and the outside diameter of the inserted ET 29 or other device. The greater this diameter difference, the more it is possible for misalignment of ET orientation, with respect to the glottic opening. To solve this problem at little expense, FIG. 7 shows an LMA 60 having the liftable bar 20 of FIGS. 3 to 5, but with additional provision of an internal ramp device 61 characterizing the inner wall of the backing plate 16'. As the ET emerges from its guidance in airway tube 14 (and the backing-plate airway inlet), the ET will have been in tracking contact with the final arc of airway-tube curvature (i.e., at eccentric offset from the central axis of airway tube 45, at entry into the air inlet of backing plate 16'), as seen with some exaggeration in the enlarged section of FIG. 8. And the compliant stress to which the ET was subjected in the course of airway-tube guidance has the effect of causing the ET to continue to track the same, although progressively straightening, path of guidance as it enters the concavity of the backing plate; this tendency is not without the penalizing effect of losing the correct orientation for passage through the glottic opening.

To enable achievement of at least an approximately correct orientation of the distal end of the ET, the ramp 61 is poised to elevate the distal end of the ET as its distal insertion progresses. One sees, from the ramp section 9—9 at which FIG. 9 is taken, that the ramp 61 has laterally flared opposite slopes, which are symmetrical about the section of FIG. 7 (designated 7—7 in FIG. 9). Not only do these flared slopes define a "V" to automatically center the ET with respect to the section flare, but, as integral parts of the ramp 61, they also bring the distal end of the ET to an elevated angle of more correct alignment with the glottic opening. Correct alignment does not necessarily require the concentric positioning of FIG. 9, in that at least the full range of diameter difference (i.e., airway-tube bore diameter, less outer diameter of the inserted endotracheal tube) is available for ramp correction of endotracheal-tube projection from the mask.

Figure 10:
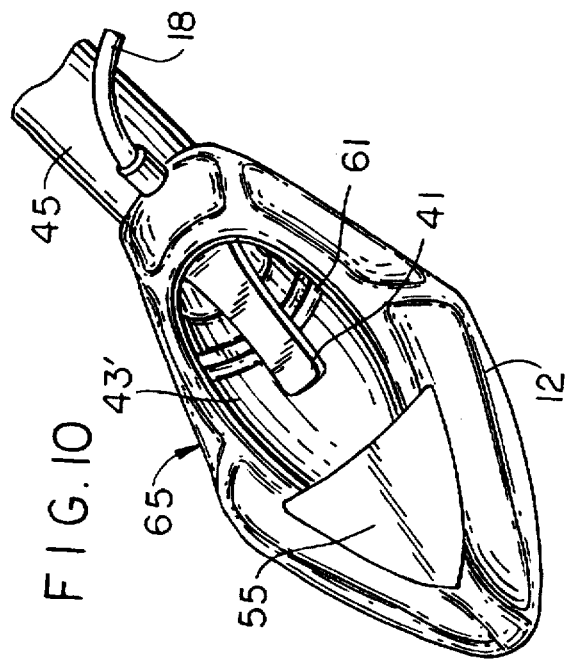
FIG. 10 is a simplified view of an LMA device of the invention, in deflated condition.

The mask 65 of FIG. 10 may in all respects be like the mask 40 of FIG. 6, except for a showing of its deflated condition, and except that, instead of the second selectively inflatable system 47, 48 of FIG. 6, the bowl concavity 43' features an integral ramp formation 61, as described in connection with FIGS. 7 and 9. The purpose of FIG. 10 is to demonstrate that upon deflation of the ring 12, the skirt 55 (which provides the safety feature of a pocket to foreclose a misdirected ET from entry into the oesophagus) also serves an important additional purpose, it being noted that even in the fully deflated condition shown, the skirt 55 remains substantially flat across its transverse span.

The additional purpose served by skirt 55 will be recognized from the fact that with careless or inadequately skilled personnel, it can occur that upon insertion of the deflated mask in the patient's throat passage, the distal end of the mask encounters the patient's epiglottis in such manner as to bend the epiglottis downward, thus potentially traumatizing the epiglottis. However, in the course of further insertion of the mask to its intended depth, the downturned epiglottis will smoothly ride the skirt 55, eventually enabling the epiglottis to at least partially enter the bowl concavity, to an extent such that upon a short manipulated retracting displacement of the LMA, the epiglottis will be engaged by the transverse proximal edge of skirt 55 and will be caused to reestablish its normal upwardly directed orientation, within the volume of bowl 43', prior to final distally directed insertional manipulation of the LMA, into its desired position of hypopharynx engagement. At this juncture, the mask will have been correctly positioned, with the epiglottis safely covered by the as-yet unactuated bar 41, and the ring 12 can be inflated, to establish its sealed engagement to the laryngeal inlet.

It will be understood that for all described embodiments of the invention, it is preferred to have ring-12 inflation accompanied by inflation of a back cushion which will serve to provide a mask-stabilizing reference to the back wall of the pharynx, thus enhancing the seal engagement of ring 12 to the laryngeal. Such a back cushion is illustratively described in U.S. Pat. No. 5,355,879, and therefore it is only illustratively and schematically indicated, by phantom profile 39 in FIGS. 5 and 7. FIG. 7 additionally indicates that the thin flexible skirt 55 longitudinally laps distal body features between the laryngeal inlet and the upper sphynctral region 27, so that in conjunction with an inflated back cushion 39 (engaged to the back wall of the pharynx) the skirt 55 will be self-conforming in its adaption to such body features, thus increasing the area of resilient engagement to the laryngeal perimeter and enhancing the effectiveness of sealed engagement of the inflated mask around the laryngeal inlet.

Figure 11:
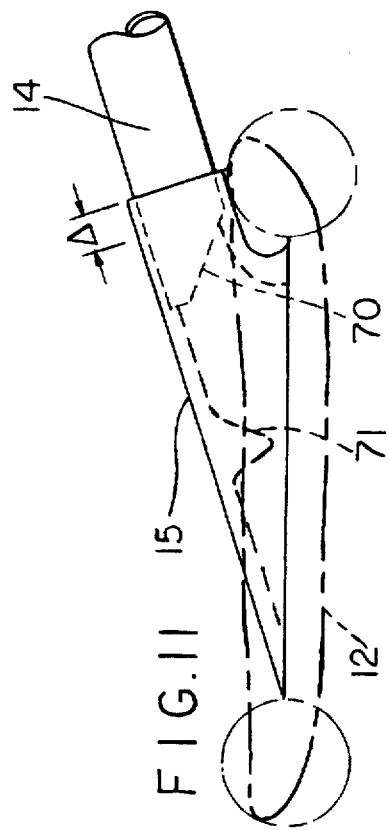
FIG. 11 is a simplified side view of a preferred relation between an airway tube and a laryngeal mask, suitable for use in all present embodiments of the invention.

FIG. 11 shows a preferred structural relation between the counterbore of the air inlet of the backing plate and the distal end of the airway tube 14 that is fitted thereto. In particular, airway tube 14 is rigid and therefore not compressible when the proximal end of the mask must be caused to enter the space between teeth of the patient's jaws, and the inlet-airway connection to plate 15 is at a relatively thickly developed proximal region of the elastomeric backing plate. To enable the mask to transiently accommodate passage of the patient's teeth, the underside of the distal end of rigid tube 14 is truncated at 70, suitably at an angle in the range 35° to 45° with respect to the airway-tube axis, the truncation being for at least half of the circumference of the distal end of the airway tube, as shown. Such a truncation enables full reception of the airway tube in the counterbore of the backing plate, as long as the depth of the counterbore is at least equal to the outer diameter of the airway tube, the preferred extent being such that a fully circumferential counterbore lap of the airway tube exists for a depth Δ of at least 20 percent of the counterbore depth, as shown. Such a structural relation will be seen to permit the operator to locally pinch the mask at the region of the counterbore and thus to compress the truncated region against elastomeric material of the mask, with sufficient transient reduction of mask thickness to permit transit of the patient's teeth. In FIG. 11, the profile of the deflated seal ring of the mask appears in heavy phantom outline, to suggest the overall thickness condition to be dealt with in the described squeezing action; the subsequently inflated condition is suggested by light phantom outlines at the proximal and distal ends of the mask.

As an alternative to the locally inflatable device 47 of FIG. 6, FIG. 11 shows use of another ramp structure 71 (shown by dashed outline) built into the bowl of the mask at substantially the longitudinal mid-section of the mask bowl. As with the V-shape of ramp 61 of FIGS. 7, 9 and 10, the transverse profile of ramp structure 71 is also preferably of V-shape, which may provide a more diverting cam action on the advancing distal end of an endotracheal tube, as compared with the epiglottic-elevating action of ramp 61 on the liftable bar 20. The ramps 61 and 71 may be used in tandem, i.e., in longitudinal succession in the bowl of the same laryngeal mask. In both of the ramps 61, 71, the transverse V-shaped profile, wherein the included angle of the V-shape is suitably in the range of 130 to 150 degrees, will be seen to provide a continuing centering action on the emerging ET tube. And since the airway tube 14 (45) of the laryngeal mask is relatively rigid and the backing-plate member 15 is relatively flexible, the described construction enables such manual manipulation of the mask via the airway tube as to enable the distal end of the ET tube to be oriented for a correct entry into the trachea via the glottic opening, even when the mask may have become "kinked" due to an anatomical abnormality.

The described invention will be seen to meet the stated objects. The advancing distal end of an endotracheal tube 29, or other instrumentality, in the course of its guided insertion via the air-supply tube 14 and backing-plate passage 17, will encounter the hinged flap or bar 20 in its at-rest position. This encounter is from an aspect which has an outwardly camming action on bar 20, to deflect in rotation about the effective hinge axis and with such engagement to the epiglottis 30 as to readily fold the epiglottis toward adjacent wall structure of the laryngeal inlet, all within and safely clearing the sealed inflatable ring 12 and skirt 55 of the LMA.

What is claimed is:

1. A laryngeal mask to facilitate ventilation of the lungs of a patient, comprising a generally elliptical ring and means for inflating/deflating the same, mask structure within and peripherally connected to said ring and having a tubular inlet-air connection adapted for externally available ventilation through an aperture in said mask structure, said aperture having an area aligned for direct passage of instrumentation inserted via said tubular inlet-air connection, a longitudinally extending central bar having hinged connection at its upper end to said mask structure via the upper end of said aperture, the hinged connection being such as to position said bar across the center of said aperture in an at-rest position and to be compliantly deflected out of said at-rest position in response to engagement by instrumentation advanced through said tubular inlet-air connection.

2. A laryngeal mask to facilitate ventilation of the lungs of a patient, comprising a generally elliptical ring and means for inflating/deflating the same, mask structure within and peripherally connected to said ring and having a tubular inlet-air connection adapted for externally available ventilation through an aperture in said mask structure, said aperture having an area aligned for direct passage of instrumentation inserted via said tubular inlet-air connection, a longitudinally extending central bar having an integrally formed compliantly yieldable hinge connection at its upper end to said mask structure via the center of the proximal upper end of said aperture, the hinge connection being such as to position said bar across the center of said aperture in an at-rest position and to be compliantly deflected out of said at-rest position in response to engagement by instrumentation advanced through said tubular inlet-air connection.

3. The laryngeal mask of claim 1, in which the distal end of said bar is free of connection to the distal lower end of said aperture.

4. The laryngeal mask of claim 3, in which the distal rim of the lower end of said aperture has a recess formation that is adapted to receive and locate said bar in its at-rest position.

5. The laryngeal mask of claim 1, in which the area within said inflatable ring is sized to receive the patient's epiglottis, with said bar in its at-rest position preventing airway closure by the epiglottis, and with the hinge connection of said bar being at least at some longitudinal offset proximally above the location of at-rest bar contact with the epiglottis, whereby an inserted ET or other instrumentation through said inlet-air connection will, on encountering contact with said bar, elevate said bar and at the same time fold the epiglottis back out of the path of advancing instrument passage.

6. The laryngeal mask of claim 1, in which said mask has laterally spaced recesses for accommodating the respective arytenoid cartilages of the patient.

7. The laryngeal mask of claim 5, in which said bar is upwardly bowed in the form of an arched surface poised for initial contact with an advancing endotracheal tube, wherein initial contact is at a region of acute-angle relationship between the directed axis of ET insertion and a tangent to the arched surface of the bar.

8. The laryngeal mask of claim 5, in which said bar is of progressively reducing effective width wherein maximum width is at the region of the effective hinge connection.

9. A laryngeal mask to facilitate ventilation of the lungs of a patient, comprising a generally elliptical ring having softly compliant peripheral engageability to a laryngeal inlet, mask structure within and peripherally connected to said ring and having a tubular inlet-air connection adapted for externally available ventilation through an aperture in said mask structure, said aperture having an area aligned for direct passage of instrumentation inserted via said tubular inlet-air connection, a longitudinally extending central bar integrally formed with said mask structure and having compliantly yieldable hinged connection at its upper end to said mask structure via the upper end of said aperture, the hinged connection being such as to position said bar across the center of said aperture in an at-rest position and to be compliantly deflected out of said at-rest position in response to engagement by instrumentation advanced through said tubular inlet-air connection.

10. In a laryngeal mask airway construction, wherein an airway tube has a distal end adapted with masking structure to provide in generally a single plane a peripherally sealed engagement to the laryngeal inlet of a patient, thereby to establish a pharyngeal side of the mask structure apart from an opposite laryngeal side of the mask, and wherein the masking structure provides a single passage for airway supply to the pharyngeal side of the mask for exclusive acute-angle communication with the laryngeal side of the mask via an airway aperture in the mask, said acute-angle communication being with respect to said plane, the improvement wherein a bar to prevent epiglottis blockage of the airway aperture is integrally formed with said masking structure and is elongate in the general direction of airway passage through the mask aperture and is so hingedly connected to the laryngeal side of said mask as, in an at-rest position thereof, to diametrically span the airway aperture of the mask and thus to provide a barrier against epiglottis blockage of airflow through the mask, said hinge connection being such that said bar is compliantly deflectable in the event of instrumentation such as an endotracheal tube being inserted via the airway tube for guidance to and through the laryngeal inlet, said compliant deflection being upon advancing-displacement contact of said bar by the inserted instrumentation, and said deflection being sufficient to deflect the epiglottis while removing said bar from interference with the airway-directed guidance of said instrumentation.

11. The improvement of claim 10, wherein ramp means constituting an integrally formed feature of said mask is so positioned in the path of instrumentation inserted via the airway tube as to deflect the instrumentation into a distally continuing path which is inclined to said plane at a greater acute angle than prior to ramp contact with the instrumentation.

12. The improvement of claim 11, in which the cross-sectional profile of said ramp means transverse to said path is V-shaped and symmetrical on opposite sides of the longitudinal plane of symmetry of the mask, whereby the V-shape serves to position the axis of advancing instrumentation in the longitudinal plane of symmetry of the mask.

13. The improvement of claim 10, in which ramp means constituting a displaceable feature of said mask is so positioned in the path of instrumentation inserted via the airway tube as to deflect the instrumentation into a distally continuing path which is inclined to said plane at a greater acute angle than prior to ramp contact with the instrumentation, said ramp means including selectively operable means for variably controlling the extent to which said ramp means extends into the path of instrumentation inserted via the airway tube, whereby to selectively control the extent to which the instrumentation is deflected by said ramp means.

14. The improvement of claim 13, in which said selectively operable means is pneumatic.

15. The improvement of claim 10, wherein the airway tube is relatively rigid and the masking structure is relatively flexible, and wherein ramp means constituting an integrally formed feature of said mask is so positioned in the path of instrumentation inserted via the airway tube as to enable deflection of the instrumentation into a distally continuing deflected path which is at a deflected angle from the direction of exit from the airway tube, said deflected angle being selectively manipulable by reason of the relatively flexible nature of the masking structure as compared to the relatively rigid nature of the airway tube, thereby enabling manipulation of the airway tube to selectively manoever the distal end of instrumentation advanced through and projecting beyond the masking structure, whereby to sense for the glottic opening and for instrumentation entry in and through the glottic opening.

13

16. The improvement of claim 15, in which the integrally formed feature has a V-shaped transverse section that is adapted to provide for advancing instrumentation of rod-like configuration a central stabilizing reference to the mask structure.

17. The improvement of claim 16, in which the integrally formed feature is at substantially the longitudinal midsection of the masking structure.

18. In a laryngeal mask airway construction, wherein a rigid airway tube has an external manipulating handle at its proximal end and is adapted at its distal end with masking structure to provide in generally a single plane a peripherally sealed engagement to the laryngeal inlet of a patient thereby to establish a pharyngeal side the mask structure apart from an opposite laryngeal side of the mask for exclusive acute-angle communication with the laryngeal side of the mask via an airway aperture in the mask, said acute-angle communication being with respect to said plane, the improvement wherein a bar to prevent epiglottis blockage of the airway aperture is integrally formed with said masking structure and is elongate in the general direction of airway passage through the mask aperture, said bar being so hingedly connected to the laryngeal side of the mask as, in an at-rest position thereof, to diametrically span the airway aperture and thus to provide a barrier against epiglottis blockage of airflow through the mask, said hinge connection being such that said bar is compliantly deflectable in the event of an endotracheal tube or other instrument being inserted via the airway tube for guidance to and through the laryngeal inlet, and said mask including pneumatically operative ramp means operative in the path of advancing displacement of the endotracheal tube to deflect the path of advancing displacement of the endotracheal tube while also deflecting said bar as well as the epiglottis.

19. The improvement of claim 18, in which actuating means for said pneumatically operative ramp means is mounted to said manipulating means.

20. The improvement of claim 19, in which said actuating means is pneumatic and has a flexible-tube connection to said ramp means.

21. The improvement of claim 18, in which said ramp means has a cross-sectional profile transverse to said path, wherein the sectional profile is V-shaped and symmetrical on opposite sides of the longitudinal plane of symmetry of the mask.

22. The improvement of claim 18, in which said mask comprises a backing plate surrounded by an inflatable ring, said backing plate being of compliant elastomeric material and having a counterbored inlet by which the distal end of the rigid airway tube is connected to the mask, the axial extent of the counterbored inlet being at least approximately the diameter of the rigid airway tube, and the distal end of the airway tube being truncated for at least half of its distal-end circumference, wherein the truncation is at an angle in the range of 35 to 45 degrees with respect to the axis of the airway tube at its distal end.

23. The improvement of claim 22, wherein the truncation is symmetrical on opposite sides of the longitudinal plane of symmetry of the mask, and wherein the truncation faces said single plane.

24. The improvement of claim 18, in which said masking structure includes a concave bowl of generally elliptical configuration wherein the concavity faces the laryngeal inlet and has distally convergent segments, and a skirt of pliant material continuously connected to said mask structure and spanning said distally convergent segments and the distal-end bowl region between said segments, to thereby define a proximally open pocket between said skirt and the distal-end region of the bowl concavity.

25. A laryngeal mask to facilitate ventilation of the lungs of a patient, comprising a generally elliptical ring with distally convergent segments and means for inflating/deflating the same to establish a peripheral engagement of the mask around the patient's laryngeal inlet, mask structure comprising a concave bowl wherein the concavity of the bowl extends between proximal and distal longitudinal ends and is adapted to face the laryngeal inlet, said bowl being within and peripherally connected to said ring and having a proximal-end tubular inlet-air connection adapted for externally available ventilation through an aperture in said mask structure, said aperture having an area aligned for direct passage of instrumentation inserted via said tubular inlet-air connection, a longitudinally extending central bar integrally formed with said mask structure and having compliantly yieldable hinged connection at its upper end to said mask structure via the upper end of said aperture, the hinged connection being such as to position said bar across the center of said aperture in an at-rest position and to be compliantly deflected out of said at-rest position in response to engagement by instrumentation advanced through said tubular inlet-air connection, and a skirt of pliant sheet material continuously connected to the adjacent distally convergent segments of said inflatable ring and thus defining a proximally open pocket between said skirt and the distal-end region of the concavity of said bowl.

26. The laryngeal mask of claim 25, in which said skirt is at longitudinal offset from said bar.

27. A tracheal-intubation device for facilitating the insertion of an endotracheal tube into the trachea of a patient, comprising:

relatively rigid guide means having a proximal end and a distal end and curved between said ends to follow the airway of a patient to a distal-end location within the pharynx and adjacent the epiglottis and in an orientation such that an inserted endotracheal tube will be directionally guided toward the glottic opening upon inserted passage beyond the distal end of said guide means; and flexibly deflectible epiglottis-lifting means hingedly connected to said guide means and normally poised across a guidance path for interception by insertional advance of an endotracheal tube, said epiglottis-lifting means being deflected by and out of the path of the advancing endotracheal tube while also lifting the epiglottis out of the path of endotracheal-tube advance to and through the glottic opening.

28. The tracheal-intubation device of claim 27, in which said relatively rigid guide means is an airway tube.

29. The tracheal-intubation device of claim 28, in which the distal end of said guide means is a laryngeal-mask formation having flexible means for establishing a peripherally sealed and stabilizing engagement to and around the laryngeal inlet.

30. The tracheal-intubation device of claim 29, (a) in which the curve of said guide means establishes a guide path in a single plane of symmetry of said guide means, (b) in which said epiglottis-lifting means is a bar that is elongate in said single plane and has lateral symmetry about said single plane, (c) in which the connection of said bar to said guide means is a compliant connection adapted to establish compliantly deflected hinge action about an effective hinge axis that is normal to said single plane of symmetry.

31. A tracheal-intubation device for facilitating the insertion of an elongate flexible instrument into the trachea of a patient, comprising:

relatively rigid guide means having a proximal end and a distal end and curved between said ends to follow the airway of a patient to a distal-end location within the pharynx and adjacent the epiglottis and in an orientation such that an inserted elongate flexible instrument will be directionally guided toward the glottic opening upon inserted passage beyond the distal end of said guide means; and flexibly deflectible epiglottis-lifting means hingedly connected to said guide means and normally poised across the guidance path for interception by insertional advance of the elongate flexible instrument, said epiglottis-lifting means being deflected by and out of the path of the advancing flexible instrument while also lifting the epiglottis out of the path of flexible-instrument advance to and through the glottic opening.

32. The tracheal-intubation device of claim 31, in which the elongate flexible instrument is an endotracheal tube.

33. The tracheal-intubation device of claim 31, in which the elongate flexible instrument is an element of an endoscopic-viewing device.

* * * * *